United States Patent
Fu et al.

(10) Patent No.: US 9,273,901 B2
(45) Date of Patent: Mar. 1, 2016

(54) MICROWAVE VACUUM-DRYING OF ORGANIC MATERIALS

(75) Inventors: Jun Fu, Port Coquitlam, CA (US);
Timothy D. Durance, Vancouver, CA (US); Parastoo Yaghmaee, Vancouver, CA (US)

(73) Assignee: EnWave Corporation, Vancouver, CA (US)

( * ) Notice: Subject to any disclaimer, the term of this patent is extended or adjusted under 35 U.S.C. 154(b) by 0 days.

(21) Appl. No.: 14/123,671

(22) PCT Filed: Jul. 12, 2012

(86) PCT No.: PCT/CA2012/000677
§ 371 (c)(1),
(2), (4) Date: Jul. 23, 2014

(87) PCT Pub. No.: WO2013/010257
PCT Pub. Date: Jan. 24, 2013

(65) Prior Publication Data
US 2014/0328867 A1    Nov. 6, 2014

Related U.S. Application Data

(60) Provisional application No. 61/509,463, filed on Jul. 19, 2011.

(51) Int. Cl.
*F26B 3/347* (2006.01)
*A61K 39/00* (2006.01)
(Continued)

(52) U.S. Cl.
CPC . *F26B 3/347* (2013.01); *A23L 3/54* (2013.01); *A61K 35/741* (2013.01); *A61K 39/00* (2013.01);
(Continued)

(58) Field of Classification Search
CPC ...... F26B 3/347; F26B 25/001; F26B 25/008; A23L 3/54; C12M 47/14; C12N 13/00; C12N 9/00; A61K 35/741; A61K 39/00
See application file for complete search history.

(56) References Cited

U.S. PATENT DOCUMENTS

| 4,320,585 A | 3/1982 | Duperret |
| 4,640,020 A | 2/1987 | Wear et al. |

(Continued)

FOREIGN PATENT DOCUMENTS

| DE | 40 36 112 A1 | 5/1992 |
| EP | 0 505 677 B1 | 9/1992 |

(Continued)

OTHER PUBLICATIONS

DE 40 36 112, Fraunhofer-Gesellschaft—English.
(Continued)

*Primary Examiner* — Jiping Lu
(74) *Attorney, Agent, or Firm* — McKee, Voorhees & Sease, PLC

(57) ABSTRACT

An apparatus (20) for dehydrating organic material in batches has a processing unit (22) having a microwave-vacuum chamber (34), an input module (28) and an output module (30), with a conveyor (54) for moving the material through the chamber on a microwave-transparent window. A material reservoir (68) is arranged to receive the material exiting the output module. A conveyor (78) external to the vacuum chamber conveys material that exits the reservoir to the input module. The vacuum chamber (34), reservoir (68) and external conveyor (78) are in fluid communication to operate at a common, reduced pressure. The organic material passes through the vacuum chamber multiple times to equilibrate and dry to the desired degree.

34 Claims, 8 Drawing Sheets

(51) Int. Cl.
*F26B 25/00* (2006.01)
*C12M 1/00* (2006.01)
*A23L 3/54* (2006.01)
*C12N 13/00* (2006.01)
*A61K 35/741* (2015.01)
*C12N 9/00* (2006.01)

(52) U.S. Cl.
CPC ............ *C12M 47/14* (2013.01); *C12N 9/00* (2013.01); *C12N 13/00* (2013.01); *F26B 25/001* (2013.01); *F26B 25/008* (2013.01)

(56) References Cited

U.S. PATENT DOCUMENTS

| | | |
|---|---|---|
| 4,664,924 A | 5/1987 | Sugisawa et al. |
| 4,882,851 A | 11/1989 | Wennerstrum et al. |
| 5,020,237 A | 6/1991 | Gross et al. |
| 5,229,010 A | 7/1993 | Fluchel |
| 5,285,581 A | 2/1994 | Walker |
| 5,946,816 A | 9/1999 | Smith |
| 7,574,816 B2 * | 8/2009 | Shivvers .................... 34/333 |
| 2010/0000110 A1 | 1/2010 | Li |
| 2010/0146806 A1 | 6/2010 | Kendall et al. |

FOREIGN PATENT DOCUMENTS

| | | |
|---|---|---|
| EP | 1 092 353 A2 | 4/2001 |
| FR | 2 768 026 A1 | 3/1999 |
| WO | 2008013947 | 1/2008 |
| WO | 2010135811 | 12/2010 |

OTHER PUBLICATIONS

EP 0 505 677, Bucher-Guyer AG—English.
EP 1 092 353, Santrade Ltd.—English.
FR 2 768 026, Societe De Developpement Industriel—English.
Enwave Corporation, PCT/CA2012/000677 filed Jul. 12, 2012, "International Preliminary Report on Patentability", date issued Jan. 21, 2014.
European Patent Office "Supplemental European Search Report," issued in connection to International Application No. EP 12 81 5492, mailed Apr. 24, 2015, 2 pages Apr. 24, 2015.

* cited by examiner

MICROWAVE VACUUM-DRYING OF ORGANIC MATERIALS

CROSS-REFERENCE TO RELATED APPLICATIONS

This is a National Phase application claiming priority to PCT/CA2012/000677 filed Jul. 12, 2012 which claims priority under 35 U.S.C. §119 to provisional application U.S. Ser. No. 61/509,463 filed Jul. 19, 2011, all of which are herein incorporated by reference in their entireties.

FIELD OF THE INVENTION

The invention pertains to apparatuses and methods for microwave vacuum-drying of organic materials, including food products and biologically-active materials such as vaccines, antibiotics, enzymes, antibodies, proteins and microorganism cultures.

BACKGROUND OF THE INVENTION

Dehydration of organic materials is commonly done in the food processing industry and in the production of biologically-active materials, to preserve the products for storage, to concentrate non-volatile components, or to create a product that is used in the dehydrated form, for example dried herbs and various kinds of chips. It is known to dehydrate food products and biologically-active materials by microwave vacuum dehydration. Examples of this in the patent literature include WO 2009/049409 A1, Durance et al., published Apr. 23, 2009, and WO 2009/033285 A1, Durance et al., published Mar. 19, 2009. Microwave vacuum-drying is a rapid method that can yield products with improved quality compared to air-dried and freeze-dried products. Because the drying is done under reduced pressure, the boiling point of water and the oxygen content of the atmosphere are lowered, so food and medicinal components sensitive to oxidation and thermal degradation can be retained to a higher degree than by air-drying. The drying process is also much faster than air- and freeze-drying. The present invention is directed to improvements in the art of microwave vacuum-drying.

SUMMARY OF THE INVENTION

According to one aspect of the invention, there is provided an apparatus for dehydrating organic material, comprising a vacuum chamber (also referred to as a drying chamber) having an inlet and an outlet for the organic material, one or more microwave generators arranged to irradiate the organic material in the vacuum chamber, means for introducing the organic material to the apparatus, means for removing the organic material from the apparatus, a first conveyor means for conveying the organic material through the vacuum chamber from the inlet to the outlet, and a circuit external to the vacuum chamber for moving material that exits the vacuum chamber outlet to the vacuum chamber inlet, the circuit comprising a material reservoir and a second conveyor means. The vacuum chamber, the material reservoir and the second conveyor means are adapted to be in fluid communication with each other for operation at a common pressure that is less than atmospheric.

According to another aspect of the invention, there is provided an apparatus for dehydrating organic material, comprising a vacuum chamber having an inlet and an outlet for the organic material, one or more microwave generators arranged to irradiate organic material in the vacuum chamber, means for introducing the organic material into the apparatus, means for removing the organic material from the apparatus, a first conveyor means for conveying the organic material through the vacuum chamber from the inlet to the outlet, a material reservoir arranged to receive organic material that exits from the outlet of the vacuum chamber, and a second conveyor means for receiving the organic material from the material reservoir and conveying it to the vacuum chamber inlet. The vacuum chamber, the material reservoir and the second conveyor means are adapted to be in fluid communication with each other for operation at a common pressure that is less than atmospheric.

According to another aspect of the invention, there is provided an apparatus for dehydrating organic material, comprising a vacuum chamber module comprising two or more vacuum chambers connected operatively together, in series or in parallel, the vacuum chamber module having an inlet and an outlet for the organic material; one or more microwave generators arranged to irradiate the organic material in the vacuum chamber module; means for introducing the organic material into the apparatus and means for removing the organic material from the apparatus; a first conveyor means for conveying the organic material through the vacuum chamber from the inlet to the outlet; and a circuit external to the vacuum chamber module for moving material that exits the outlet to the inlet, the circuit comprising a material reservoir and a second conveyor means. The vacuum chamber module, the material reservoir and the second conveyor means are adapted to be in fluid communication with each other for operation at a common pressure that is less than atmospheric.

According to another aspect of the invention, there is provided a method of dehydrating an organic material, that is, of reducing its moisture content to a desired level, using an apparatus having a vacuum chamber, a microwave generator and a material reservoir, comprising the steps of introducing the organic material into the apparatus, reducing the pressure in the vacuum chamber and the material reservoir to a pressure less than atmospheric, conveying the organic material from the material reservoir to an inlet of the vacuum chamber under the reduced pressure, conveying the organic material through the vacuum chamber under the reduced pressure, from the inlet to an outlet, while irradiating the organic material in the vacuum chamber, and transferring the organic material from the vacuum chamber outlet to the material reservoir. This partly-dried organic material is recycled through the vacuum chamber one or more times to dehydrate it to the desired degree. It is then removed from the apparatus.

The organic material is dehydrated in batches, rather than in a continuous process. Drying by batch mode is preferred in some manufacturing processes, for example where fermentation or other pre-drying steps must be carried out in batch mode. The apparatus has a material reservoir and the maximum batch size is the capacity of the reservoir. This capacity can be substantially more than the amount of material that can be accommodated at one time within the drying chamber, i.e. the amount of organic material that fills the conveyor belt transporting the material through the drying chamber. Smaller batches can also be processed using the invention, for example a batch equal to the amount of product that fills the conveyor belt once. In the invention, the organic material is cycled through the drying chamber more than one time without exposing it to ambient pressure. Where the material being dehydrated is a frozen material, it stays frozen throughout the dehydration process, as it is maintained under reduced pressure even when it is not in the microwave field, i.e. when it is in the reservoir and in the second conveyor means. Also, because the batch of material being dried may pass through the drying chamber many times during the total batch processing time, the material can equilibrate and mix such that the final residual moisture in the final product is more homogeneous.

Examples of materials suitable for dehydration by the invention include fruit, either whole, puree or pieces, either frozen or un-frozen, including banana, mango, papaya, pineapple, melon, watermelon, pomegranate, apples, pears, cherries, berries, peaches, apricots, plums, grapes, oranges, lemons, grapefruit; vegetables, either fresh or frozen, whole, puree or pieces, including peas, beans, corn, carrots, tomatoes, peppers, herbs, potatoes, beets, turnips, squash, onions, garlic; fruit and vegetable juices; pre-cooked grains including rice, oats, wheat, barley, corn, flaxseed; hydrocolloid solutions or suspensions, vegetable gums; frozen liquid bacterial cultures, probiotics, food culture, vaccines, enzymes, protein isolates; amino acids; injectable drugs, pharmaceutical drugs, natural medicinal compounds, antibiotics, antibodies; composite materials in which a hydrocolloid or gum surrounds and encapsulates a droplet or particle of a relatively less stable material as a means of protecting and stabilizing the less sensitive material; meats, fish and seafoods, either fresh or frozen, either whole, puree or pieces; dairy products such as milk, cheese, whey proteins isolates and yogurt; and moist extracts of fruits, vegetables and meats.

These and other aspects and features of the invention will be apparent from the following description and drawings of the specific embodiments.

DETAILED DESCRIPTION OF THE PREFERRED EMBODIMENTS

Figure 1:
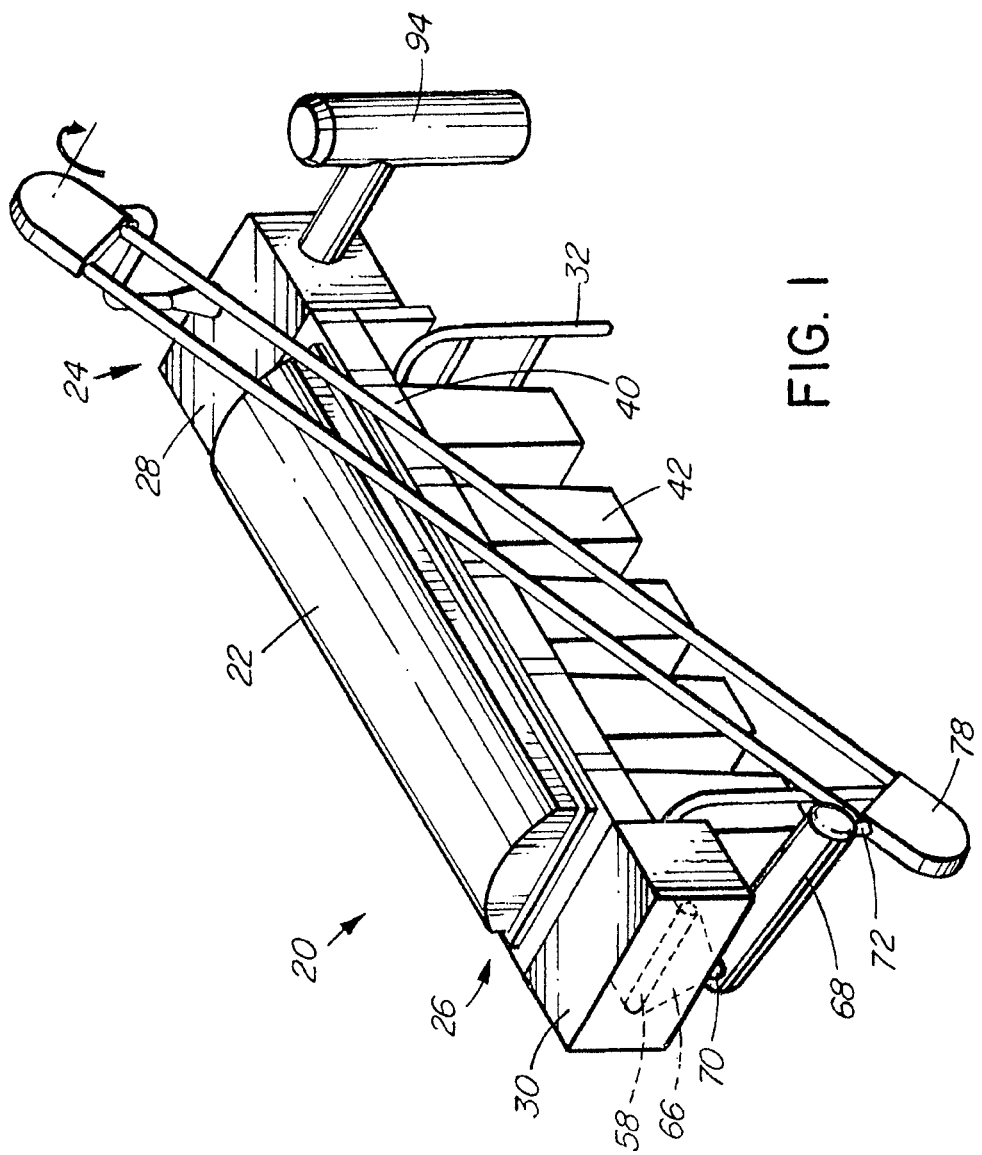
FIG. 1 is an isometric view of an apparatus according to one embodiment of the invention.
Figure 2:
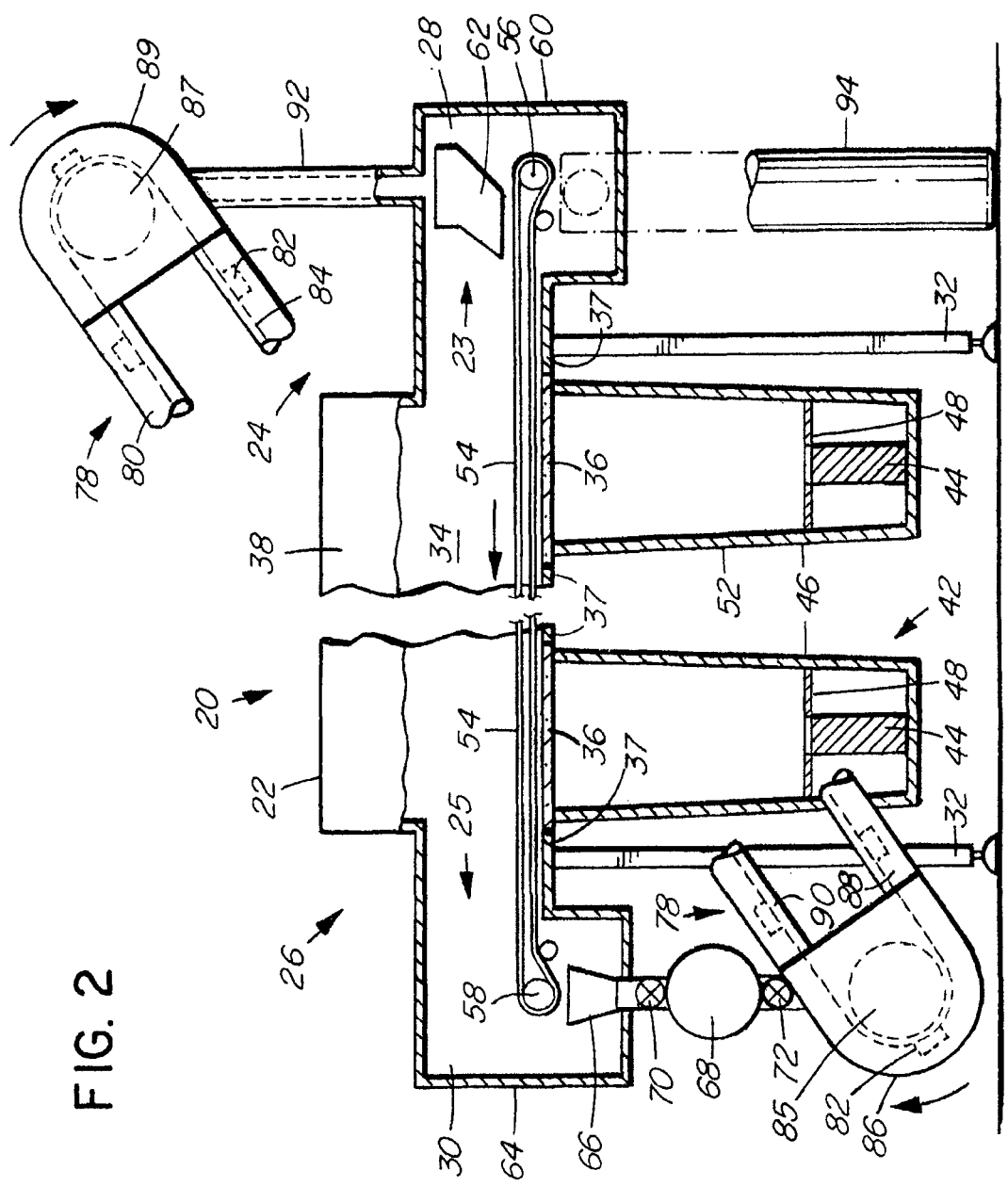
FIG. 2 is a side elevational view thereof, partly in section.
Figure 3:
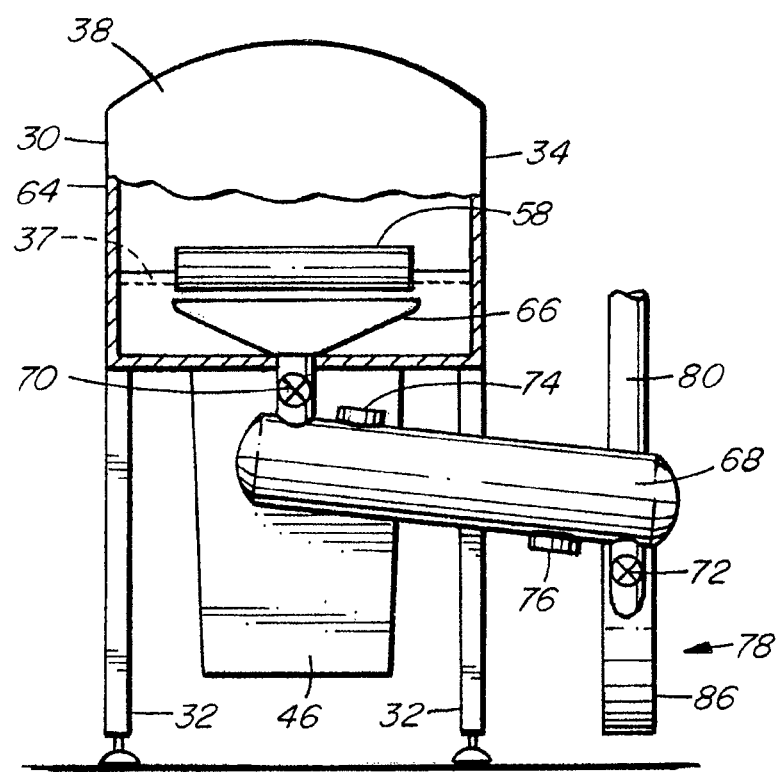
FIG. 3 is an elevational view, partly in section, of the output end thereof.
Figure 4A:
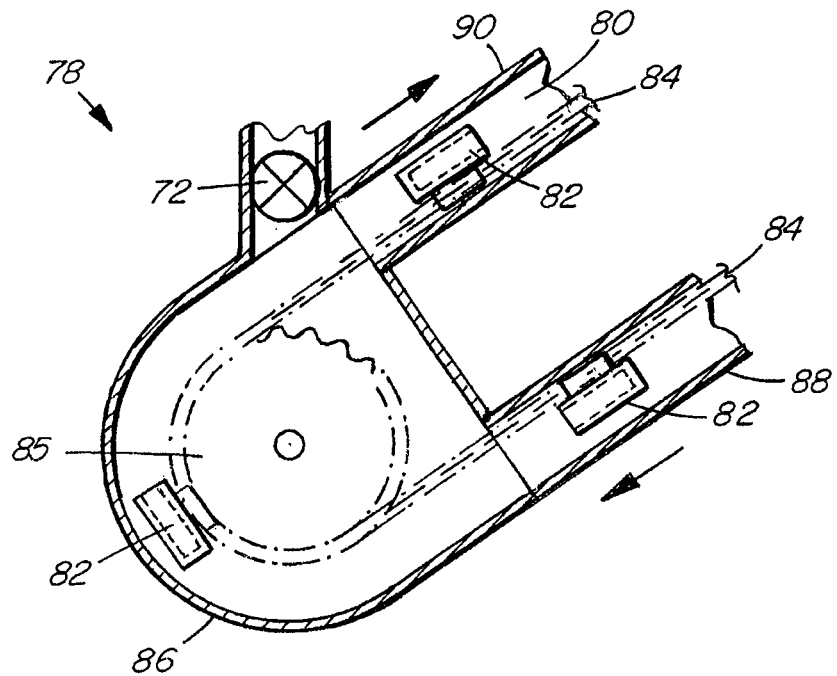
FIGS. 4A and B are elevational views, partly in section, of the lower and upper ends of the external conveyor.
Figure 4B:
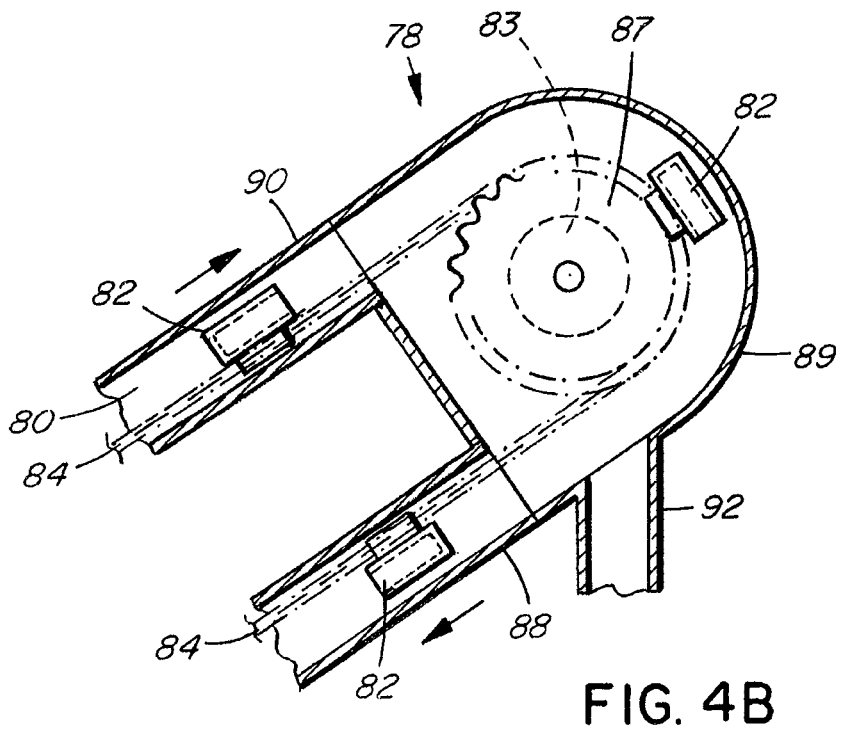

In the following description and in the drawings, corresponding and like parts are identified by the same reference characters.

Referring first to FIGS. 1 to 4, the dehydrating apparatus 20 comprises a processing unit 22, in which organic material is microwave vacuum-dried. The unit has an input end 24 and an output end 26, with an input module 28 at the input end and an output module 30 at the output end. The processing unit 22 is supported on a frame 32.

A vacuum chamber (sometimes referred to herein as a drying chamber) 34 extends the length of the processing unit 22, from an inlet 23 to an outlet 25. One or more microwave-transparent windows 36, made of Teflon or other microwave-transparent material, form at least part of the bottom wall of the vacuum chamber. The vacuum chamber has a cover 38 and side walls 40. Microwave chamber modules 42 are arranged below the window 36, there being five such modules in the illustrated embodiment. Each module has one or more microwave generators 44 and a microwave chamber 46. Each microwave chamber has side walls 52 and a floor 48, each chamber accommodating a respective microwave generator 44. Alternatively, each microwave chamber may accommodate two, three or more generators. The microwave-transparent window 36 forms the top wall of the microwave chambers 46. A separate window 36 may be provided for each microwave chamber 46, separated by panels 37. The microwave chambers are not sealed from the atmosphere and are thus air-filled and at atmospheric pressure.

A microwave-transparent conveyor belt 54 for transporting the organic material through the vacuum chamber extends along the window 36 and panels 37. The conveyor belt extends into the input and output modules 28, 30, and forms a continuous loop. The belt 54 runs over a conveyor roller 56 in the input module, which is rotated by a motor (not shown) to drive the belt, and over a roller 58 in the output module 30, with the return path of the belt being between its forward path and the microwave-transparent window 36. The belt in its forward path thus lies on the belt in its return path, which in turn lies on the windows 36 and panels 37.

The input module 28 has a housing 60, fastened and sealed to the input end 24 of the processing unit. The interior of the input module is open to the vacuum chamber 34 and is accordingly at reduced pressure during operation of the apparatus. A chute 62 is supported in the input module to receive organic material dropped into it, as described below, and deposit that material onto the conveyor belt 54 for transport through the vacuum chamber.

The output module 30 includes a housing 64 fastened and sealed to the output end 26 of the processing unit 22. The output module is open to the vacuum chamber and is thus at reduced pressure during operation of the apparatus. A chute 66 is positioned in the output module 30 below the roller 58 to receive material that falls off the output end of the conveyor belt, over the roller 58. A material reservoir 68 is positioned below and is connected to the output module to receive the organic material from the chute 66. The material reservoir 68 is a generally cylindrical tank which slopes downward as it extends laterally from the output module. At its upper end it is connected to the output module and at its lower end to a material conveyor external to the vacuum chamber, as described below. The material reservoir is open to the output module and is accordingly at reduced pressure during operation of the apparatus. The material reservoir has a valve 70, 72 at each respective end thereof, and a pressure release valve (not shown), permitting it to be sealed from the vacuum system and brought to atmospheric pressure for the purposes of introducing into it the organic material to be dried and removing dried material. The material reservoir has the capacity to hold a substantially larger volume of organic material than could be held on a length of the conveyor belt within the vacuum chamber. A loading port 74 and an unloading port 76, both with valves, provide means for the introduction and removal respectively of material when the reservoir is at atmospheric pressure.

A material conveyor 78 is provided to transport the organic material from the reservoir to the input module, external to the vacuum chamber. The material conveyor 78 comprises a sealed tube 80 arranged as a continuous loop, with cups 82 carried by a chain 84 inside the tube 80 to receive, transport and deposit the material. The chain is engaged by a sprocket 85 within a hub 86 at the lower end of the conveyor 78, and by a sprocket 87 in a hub 89 at the upper end of the conveyor. The upper sprocket 87 is attached to a drive motor 83. The tube 80 is arranged to have a lower section 88 and an upper section 90, connected by U-shaped paths within the hubs 86, 89. At the top end of the tube 80, a conduit 92 connects the tube 80 to the input module 28. Within the tube, the cups 82 are arranged so as to pick up material that drops from the reservoir into the lower hub 86, carry it through the upper section 90 of the tube, and then invert and drop their contained material as they move around the curved path from the upper section 90 to the lower section 88 of the tube. This dropped material passes into and through the conduit 92 under the force of gravity and is received in the input chute 62, from which it is deposited onto the conveyor belt 54. The tube 80 is open to the material reservoir and the input module 28 and is thus at reduced pressure during operation of the apparatus.

The dehydrating apparatus includes a vacuum pump (not shown) operatively connected to the condenser 94. The condenser is operatively connected to the vacuum chamber via the input module. It condenses water vapor produced during dehydration of the organic material. The apparatus 20 includes a refrigeration unit (not shown) comprising a compressor, cooling fan and refrigerant pump, connected to convey refrigerant to the condenser 94 and thus maintain the condenser at a desired temperature.

A water load is provided at the upper part of the vacuum chamber 34 to absorb microwave energy and thus prevent reflection of microwaves in the vacuum chamber. This is accomplished by microwave-transparent water tubing (not shown) under the cover 38 of the vacuum chamber. Water is pumped through the tubing by a pump.

The apparatus 20 includes a programmable logic controller (PLC), programmed and connected to control the operation of the system, including controlling the drive motors, the microwave generators, the vacuum pump and the refrigerant pump.

The dehydrating apparatus 20 operates according to the following method. A batch of organic material to be dehydrated is introduced into the material reservoir 68 through the loading port 74, and the port is then sealed. The vacuum pump, refrigerant pump, water pump, microwave generators and the motors to drive the conveyor belt 54 and the conveyor chain 84 are actuated, all under the control of the PLC. Since the valves 70, 72 are open, the full system is brought to reduced pressure, including the vacuum chamber 34, the output module 30, the reservoir 68, the conveyor 78 and the input module 28. Pressure within the system may be reduced to a pressure in the range of about 0.01 to 100 Torr, alternatively 0.1 to 30 Torr. The organic material, for example in granular form, may be introduced in the frozen state, and, due to the reduced pressure in the system, it remains in the frozen state throughout the process, the water therein being removed by sublimation rather than evaporation. The organic material in the reservoir 68 spills into the lower hub 86 of the conveyor 78 under the force of gravity, and is carried by the conveyor cups 82 through the upper section 90 of the tube 80 and is dropped into the conduit 92. It is then guided by the input chute 62 to the conveyor belt 54. Within the vacuum chamber 34, the material is partly dehydrated by the radiation from the microwave generators that passes through the windows 36. The belt 54 is operated at such speed, and the generators 44 at such power level, that the organic material is not fully dehydrated during one pass through the vacuum chamber. The partly-dried material is dropped off the output end of the conveyor belt into the chute 66, depositing it in the material reservoir 68. The cycle is repeated, with the partly-dried material being conveyed from the reservoir to the input module for another traverse of the vacuum chamber, further drying it. Depending on the nature of the material, the operating conditions and the batch size, i.e. the volume of material first introduced into the reservoir, additional drying cycles may be required. For example, the material may require eight hours of treatment in the vacuum chamber to dry it to the desired degree, and the conveyor belt 54 may be operated at a speed such that a single traverse through the vacuum chamber is made in one hour; the apparatus is then operated so that the material is given eight cycles of drying.

Once the material is dehydrated to the desired degree, for example to a moisture content in the range of about 0.5 to 4%, the valve 72 is shut and the material remaining in the conveyor 78 and on the conveyor belt is processed and emptied into the reservoir. The valve 70 is then closed, sealing the reservoir from the vacuum system, the pressure release valve on the reservoir is opened, and the dried material is removed via the outlet port 76.

Various arrangements of the vacuum chamber and microwave generators can be employed in the invention. For example, the generators may be above the vacuum chamber or on the side of the vacuum chamber, rather than below it as in the illustrated embodiment, and the microwave-transparent window may be above the belt, rather than below it.

It will be appreciated that the material reservoir need not be positioned at the output end of the vacuum chamber. The reservoir can be positioned anywhere in the circuit between the outlet of the vacuum chamber and the inlet thereof, externally to the vacuum chamber. Its location at the output end in the embodiment of FIGS. 1 to 4 is a matter of operator convenience. In the embodiment of the invention illustrated in FIGS. 5 and 6, the dehydration apparatus 100 differs from the dehydration apparatus 20 in that the reservoir 68 is positioned between the upper hub 89 of the conveyor 78 and the input module 28. At the output end 26 of the vacuum chamber, the output chute 66 is connected by a conduit 67 directly to the lower hub 86 of the conveyor 78, to convey material that exits the vacuum chamber outlet 25 to the lower hub 86. At the input end 24 of the vacuum chamber, material carried by the conveyor 78 is dropped into the reservoir 68, from which it falls, under the force of gravity, into the input chute 62, passing into the inlet 23 of the vacuum chamber.

The dehydrating apparatus 100 operates according to essentially the same method as described above for the dehydrating apparatus 20, except that the organic material loaded into the reservoir 68, falls directly into the input chute 62 and onto the conveyor belt 54 to be carried through the vacuum chamber; and at the output end 26, the organic material is dropped into the output chute 66 and into the lower hub 86, to be carried by the conveyor 78 back to the material reservoir 68.

Referring next to FIGS. 7(*a*) to (*d*), the invention also includes embodiments in which a vacuum chamber module comprises two or more vacuum chambers, operatively connected together, in series or in parallel.

FIGS. 7(*a*), (*b*) and (*c*) are schematic illustrations of dehydration apparatuses 200, 202, 204 in which the vacuum chambers 34A and 34B are connected together in series to form a vacuum chamber module 222. Organic material for drying that exits the outlet end 26A of the first vacuum chamber 34A is fed by the conveyor 54, which extends, under reduced pressure, through both vacuum chambers, into the inlet end 23B of the second vacuum chamber 34B. In the embodiment of FIG. 7(*a*), the material reservoir 68 is at the outlet end of the second vacuum chamber 34B, and the external conveyor 78 connects the reservoir 68 to the inlet end 23A of the first vacuum chamber 34A.

In the apparatus 202 of FIG. 7(*b*), the material reservoir 68 is located at the inlet end 23A of the first vacuum chamber 34A, and the external conveyor 78 connects the outlet end 26B of the second vacuum chamber 34B to the reservoir.

Figure 7A:
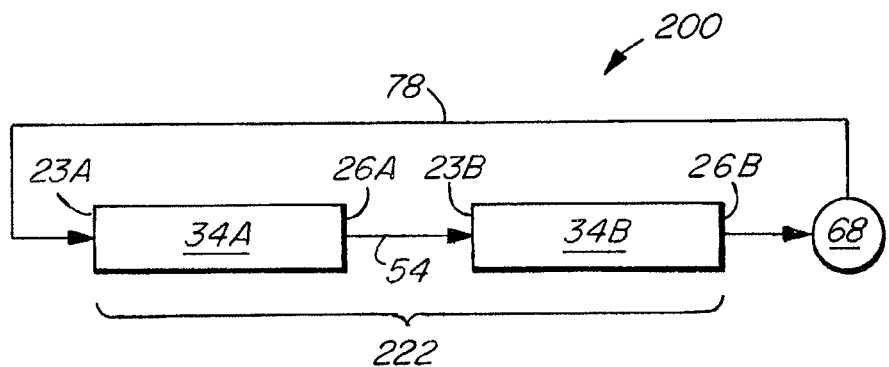
FIGS. 7(a) to (d) are schematic views of embodiments of the dehydrating apparatus having a vacuum chamber module which comprises two vacuum chambers.
Figure 7B:
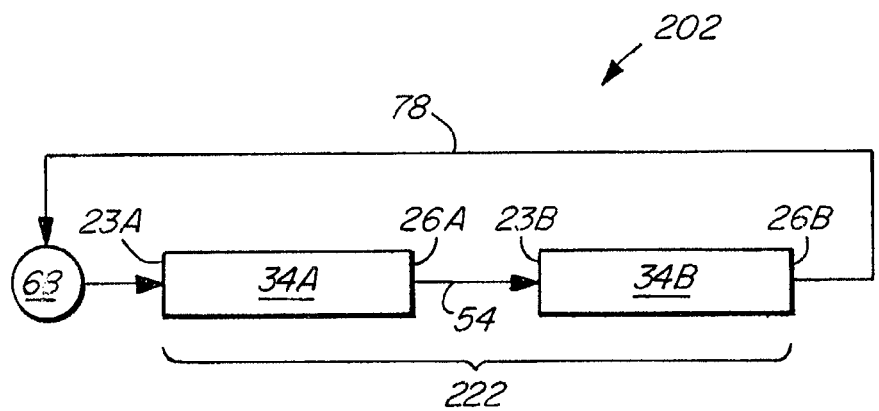
Figure 7C:
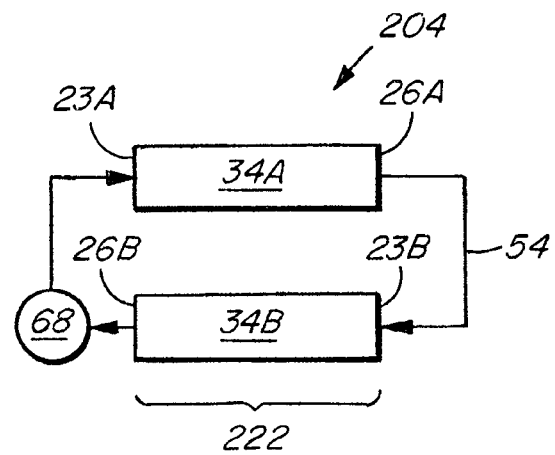

In the apparatus 204 of FIG. 7(c), the vacuum chambers 34A and 34B of the module 222, connected in series, are arranged at an orientation to each other of 180 degrees, such that the outlet end 26B of the second vacuum chamber 34B is proximate to the inlet end 23A of the first vacuum chamber 34A. The reservoir 68 is located at the outlet end 26B of the second vacuum chamber 34B, and the external conveyor 78 connects the reservoir to the inlet end 23A of the first vacuum chamber 34A. Alternatively, the reservoir may be located at the inlet 23A of the first vacuum chamber. Alternatively, the first and second vacuum chambers of the module may be oriented at other angles to each other, for example at 90 degrees.

Figure 7D:
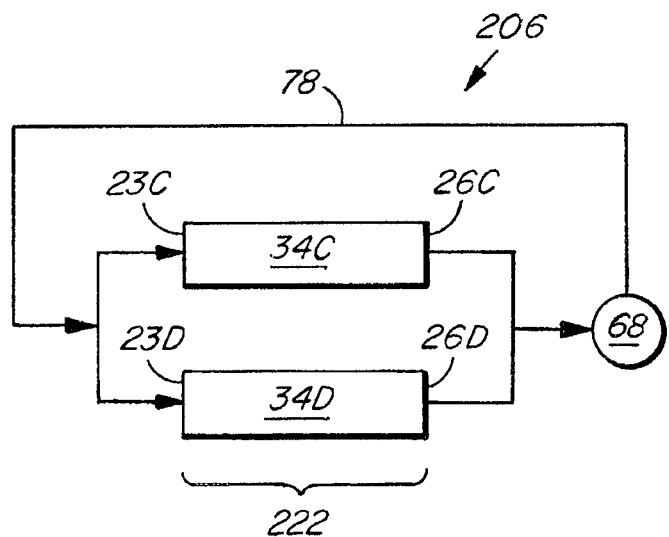

In the apparatus 206 of FIG. 7(d), the vacuum chambers 34C and 34D of the module 222 are arranged in parallel, connected to a common material reservoir 68 at the outlet ends 26C and 26D of the vacuum chambers. The material conveyor 78 connects the reservoir to the inlet ends 23C, 23D, of the vacuum chambers. Material to be dried is cycled, all under pressure, through the vacuum chambers 34C, 34D, into the reservoir and then back to the inlets 23C, 23D of the vacuum chambers, multiple times. Alternatively, the reservoir may be located at the inlet end 23C, 23D of the parallel vacuum chambers.

The vacuum chamber modules 222 may comprise more than two vacuum chambers, for example three or more, arranged in series or in parallel, or a combination of both arrangements.

It is to be understood that, although particular means for performing certain functions of the apparatus, or particular structures or steps, have been described above in respect of the preferred embodiments, various other means, structures and steps may be employed in the apparatus and method of the invention. Examples of this include the following.

(i) The means for conveying the organic material across the microwave transparent window can include means such as vibration of the window, sloping the window and using gravity, mechanical pushers, etc.

(ii) The means for reducing the pressure in the vacuum chamber can include any means for applying a vacuum to the vacuum chamber, such as connection to a central vacuum system of a plant.

Figure 5:
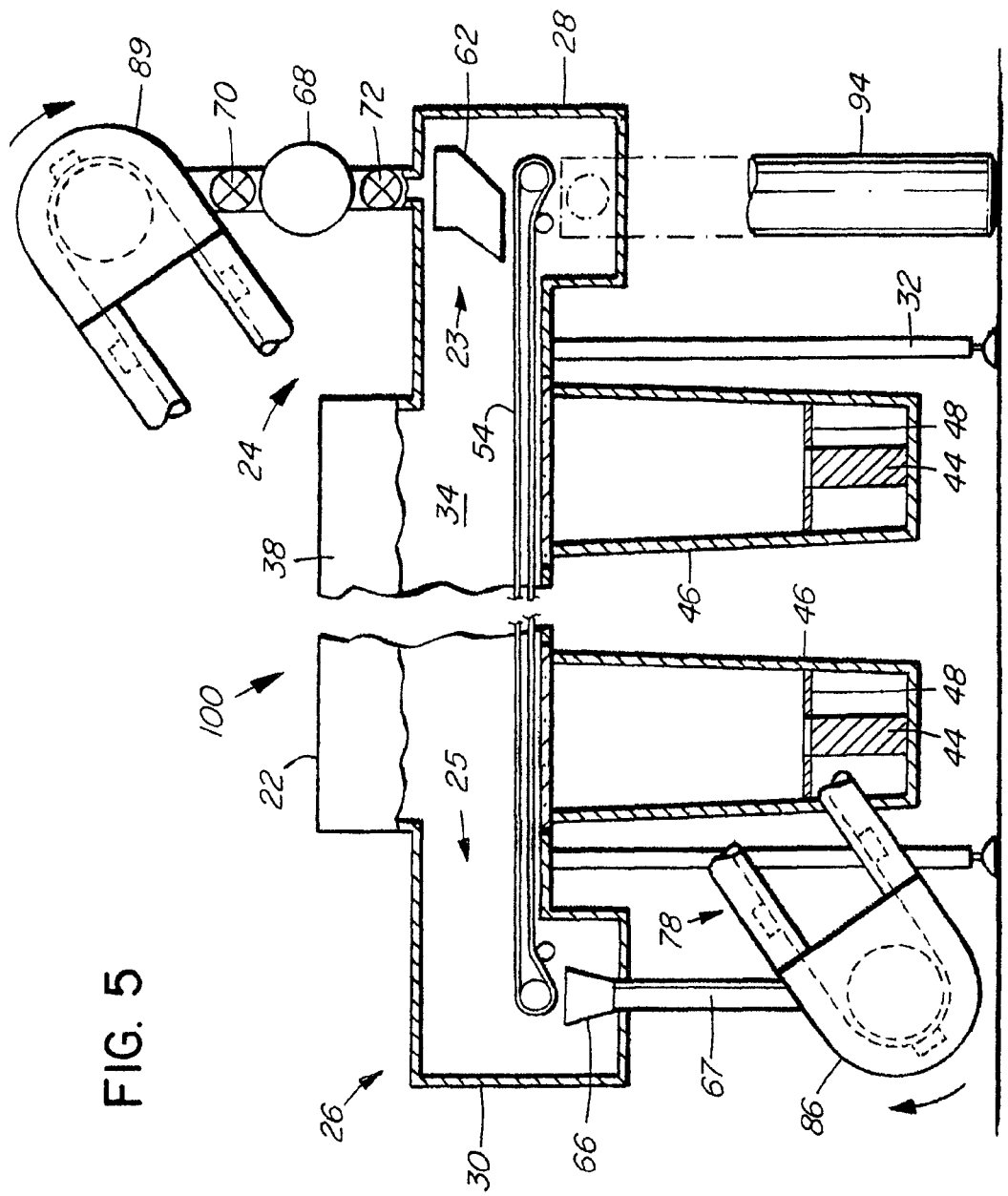
FIG. 5 is a side elevational view, partly in section, of a second embodiment of the apparatus.
Figure 6:
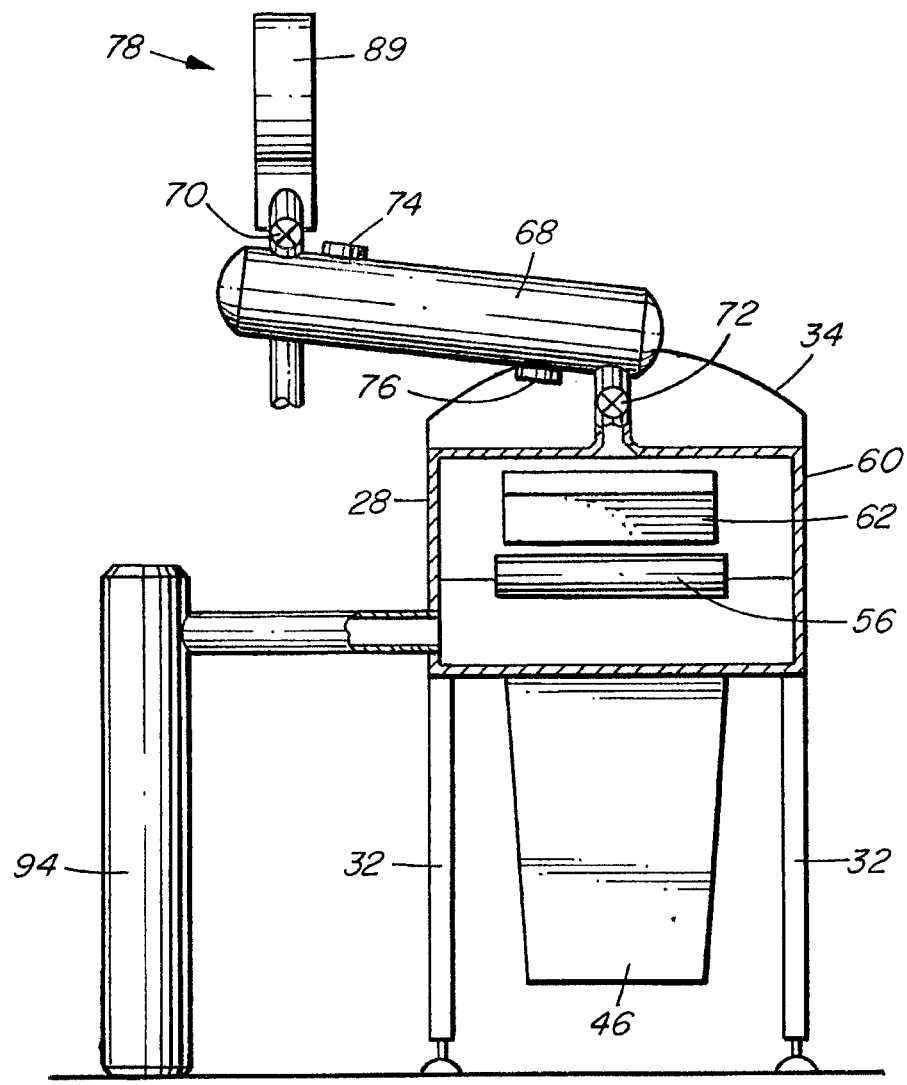
FIG. 6 is an elevational view, partly in section, of the input end of the apparatus of FIG. 5.

(iii) The means for conveying the organic material externally to the drying chamber, e.g. from the reservoir to the input module for the embodiment of FIGS. 1 to 4, or from the output module to the reservoir for the embodiment of FIGS. 5 and 6, can include any practical means for moving a solid material from a relatively lower elevation to a relatively higher elevation, while maintaining the material under reduced pressure. For example, a flexible or inflexible tube, or a combination of both, connecting the reservoir and the input module may be moved mechanically or manually so as to lift it, and the material in it, to a higher elevation and thus drop the material into the input module; or a vibrator and a conveyor belt, or a vibrator and a flexible tube, may be used.

EXAMPLE 1

Batches of organic materials that included frozen food culture, frozen probiotics and frozen enzymes were dehydrated in an apparatus of the type shown in FIGS. 1-4. The drying chamber was 4.6 meters long. The material reservoir volume was 20 liters. The batch sizes were in the range of 10 kg to 25 kg. The initial moisture content of the organic materials was in the range of 65% to 90%. The conveyor was operated at speeds in the range of 120-270 mm/min. The microwave power output was in the range of 4.5 kW to 9.0 kW. The drying chamber was operated at pressures in the range of 20-150 mTorr and at temperatures in the range of –40 degrees C. to 30 degrees C. The materials were passed through the drying chamber once every 30 minutes or 45 minutes. The total drying times were in the range of 6 to 10 hours. The materials were dried to final moisture contents in the range 0.8% to 1.5%.

EXAMPLE 2

A batch of frozen probiotic having an initial moisture content of 67% was dehydrated. The conveyor belt was operated at speeds in the range of 120-150 mm/min. The average microwave power output was 5.14 kW. The batch size was 15.25 kg. The drying chamber was operated at pressures in the range of 45-150 mTorr. The initial temperature was –38.5 degrees C. and the final temperature was 28.5 degrees C. The total drying time was 10.25 hours and the cycle time was 30 minutes. The material was dried to a final moisture content of 1.1+/–0.07%. The final weight of the dehydrated material was 4.7 kg.

As will be apparent to those skilled in the art in the light of the foregoing disclosure, many alterations and modifications are possible in the practice of this invention without departing from the scope thereof. Accordingly, the scope of the invention is to be construed in accordance with the following claims.

The invention claimed is:

1. An apparatus for dehydrating organic material, comprising:
   (a) a vacuum chamber having an inlet and an outlet for the organic material;
   (b) a microwave generator arranged to irradiate the organic material in the vacuum chamber;
   (c) means for introducing the organic material into the apparatus;
   (d) a first conveyor means for conveying the organic material through the vacuum chamber from the inlet to the outlet;
   (e) a circuit external to the vacuum chamber for moving the organic material that exits the vacuum chamber outlet to the vacuum chamber inlet, the circuit comprising a material reservoir and a second conveyor means;
   (f) means for removing the organic material from the apparatus;
   (g) the vacuum chamber, the material reservoir and the second conveyor means being adapted to be in fluid communication with each other for operation at a common pressure that is less than atmospheric; and
   (h) means for reducing pressure in the vacuum chamber, the material reservoir and the second conveyor means.

2. An apparatus according to claim 1, wherein the reservoir is positioned to receive the organic material from the vacuum chamber outlet, and the second conveyor means is positioned to receive organic material from the reservoir.

3. An apparatus according to claim 2, wherein the material reservoir slopes downward from the vacuum chamber outlet towards the second conveyor means.

4. An apparatus according to claim 1, wherein the second conveyor means is positioned to receive the organic material from the vacuum chamber outlet, and the reservoir is positioned to receive the organic material from the second conveyor means.

5. An apparatus according to claim 1, further comprising means for selectively sealing the material reservoir from the vacuum chamber and the second conveyor means.

6. An apparatus according to claim 1, wherein the means for introducing material into the apparatus comprises a loading port in the material reservoir.

7. An apparatus according to claim 1, wherein the means for removing the organic material comprises means to close the fluid communication between the material reservoir and the vacuum chamber and the second conveyor means, and a dehydrated material unloading port in the material reservoir.

8. An apparatus according to claim 1, wherein the second conveyor means is arranged to convey the material from a relatively lower elevation to a relatively higher elevation.

9. An apparatus according to claim 1, wherein the second conveyor means comprises a tube forming a continuous loop and material carriers arranged for movement through the tube.

10. An apparatus according to claim 1, wherein the first conveyor means is a belt.

11. An apparatus for dehydrating organic material, comprising:
   (a) a vacuum chamber having an inlet and an outlet for the organic material;
   (b) a microwave generator arranged to irradiate the organic material in the vacuum chamber;
   (c) means for introducing the organic material into the apparatus;
   (d) a first conveyor means for conveying the organic material through the vacuum chamber from the inlet to the outlet;
   (e) a material reservoir arranged to receive the organic material from the outlet of the vacuum chamber;
   (f) a second conveyor means for receiving the organic material from the material reservoir and conveying it to the vacuum chamber inlet;
   (g) means for removing the organic material from the apparatus;
   (h) the vacuum chamber, the material reservoir and the second conveyor means being adapted to be in fluid communication with each other for operation at a common pressure that is less than atmospheric; and
   (i) means for reducing pressure in the vacuum chamber, the material reservoir and the second conveyor means.

12. An apparatus for dehydrating organic material, comprising:
   (a) a vacuum chamber module comprising two or more vacuum chambers connected operatively together, in series or in parallel, the vacuum chamber module having an inlet and an outlet for the organic material;
   (b) a microwave generator arranged to irradiate the organic material in the vacuum chamber module;
   (c) means for introducing the organic material into the apparatus;
   (d) a first conveyor means for conveying the organic material through the vacuum chamber module from the inlet to the outlet;
   (e) a circuit external to the vacuum chamber module for moving the organic material that exits the outlet to the inlet, the circuit comprising a material reservoir and a second conveyor means;
   (f) means for removing the organic material from the apparatus;
   (g) the vacuum chamber module, the material reservoir and the second conveyor means being adapted to be in fluid communication with each other for operation at a common pressure that is less than atmospheric; and
   (h) means for reducing pressure in the vacuum chamber module, the material reservoir and the second conveyor means.

13. An apparatus according to claim 12, wherein the reservoir is positioned to receive the organic material from the vacuum chamber module outlet, and the second conveyor means is positioned to receive organic material from the reservoir.

14. An apparatus according to claim 13, wherein the material reservoir slopes downward from the vacuum chamber outlet towards the second conveyor means.

15. An apparatus according to claim 12, wherein the second conveyor means is positioned to receive the organic material from the vacuum chamber module outlet, and the reservoir is positioned to receive the organic material from the second conveyor means.

16. An apparatus according to claim 12, further comprising means for selectively sealing the material reservoir from the vacuum chamber module and the second conveyor means.

17. An apparatus according to claim 12, wherein the means for introducing material into the apparatus comprises a loading port in the material reservoir.

18. An apparatus according to claim 12, wherein the means for removing the organic material comprises means to close the fluid communication between the material reservoir and the vacuum chamber module and the second conveyor means, and a dehydrated material unloading port in the material reservoir.

19. An apparatus according to claim 12, wherein the second conveyor means is arranged to convey the material from a relatively lower elevation to a relatively higher elevation.

20. An apparatus according to claim 12, wherein the second conveyor means comprises a tube forming a continuous loop and material carriers arranged for movement through the tube.

21. An apparatus according to claim 12, wherein the first conveyor means is a belt.

22. An apparatus according to claim 12, wherein the vacuum chambers are connected operatively together in series.

23. An apparatus according to claim 12, wherein the vacuum chambers are connected operatively together in parallel.

24. A method of dehydrating an organic material using an apparatus having a vacuum chamber, a microwave generator and a material reservoir, comprising the steps of:
   (a) introducing the organic material into the apparatus;
   (b) reducing the pressure in the vacuum chamber and the material reservoir to a pressure less than atmospheric;
   (c) conveying the organic material from the material reservoir to an inlet of the vacuum chamber, under the reduced pressure;
   (d) conveying the organic material through the vacuum chamber under the reduced pressure, from the inlet to an outlet, while irradiating the organic material in the vacuum chamber by the microwave generator;
   (e) transferring the organic material from the outlet to the material reservoir;
   (f) repeating steps (c) to (e) one or more times to dehydrate the organic material; and
   (g) removing the dehydrated organic material from the apparatus.

25. A method according to claim 24, wherein the conveying of step (c) moves the organic material from a relatively lower to a relatively higher elevation.

26. A method according to claim 24, wherein the method is operated in a batch mode.

27. A method according to claim 24, wherein, in step (a), the material is introduced into the material reservoir.

28. A method according to claim 24, wherein, in step (g), the dehydrated organic material is removed from the material reservoir.

29. A method according to claim 24, wherein the pressure is reduced to 0.01 to 100 Torr.

30. A method according to claim 24, wherein the pressure is reduced to 0.1 to 30 Torr.

31. A method according to claim 24, wherein the organic material comprises one of a fruit, a vegetable, a fruit juice, a vegetable juice, a pre-cooked grain, a bacterial culture, a vaccine, an enzyme, a protein isolate, a hydrocolloid, an injectable drug, a pharmaceutical drug, an antibiotic, an antibody, meat, fish, seafood, milk, cheese, whey protein isolate, yogurt, a fruit extract, a vegetable extract and a meat extract.

32. A method according to claim 24, wherein the organic material is frozen.

33. A method according to claim 24, wherein the organic material is encapsulated in a hydrocolloid.

34. A method according to claim 24, wherein the organic material is granular.

\* \* \* \* \*